(12) United States Patent
Horn

(10) Patent No.: US 8,597,629 B1
(45) Date of Patent: Dec. 3, 2013

(54) ARTIFICIAL TEAR COMPOSITIONS COMPRISING A COMBINATION OF NONIONIC SURFACTANTS

(71) Applicant: GNT, LLC, Dan Point, CA (US)

(72) Inventor: Gerald Horn, Deerfield, IL (US)

(73) Assignee: Premium Ocular Solutions LLC., Coronado, CA (US)

( * ) Notice: Subject to any disclaimer, the term of this patent is extended or adjusted under 35 U.S.C. 154(b) by 0 days.

(21) Appl. No.: 13/924,214

(22) Filed: Jun. 21, 2013

(51) Int. Cl.
*A61P 27/04* (2006.01)
*A61P 27/02* (2006.01)
*A61K 9/08* (2006.01)
*A61K 47/00* (2006.01)
*A61K 47/38* (2006.01)
*A61K 9/00* (2006.01)

(52) U.S. Cl.
CPC .................. *A61K 9/0048* (2013.01); *A61K 9/08* (2013.01); *A61K 47/00* (2013.01); *A61K 47/38* (2013.01)
USPC ........................................ 424/78.04; 514/781

(58) Field of Classification Search
None
See application file for complete search history.

*Primary Examiner* — Kevin S Orwig
(74) *Attorney, Agent, or Firm* — Wood, Phillips, Katz, Clark & Mortimer

(57) ABSTRACT

The invention provides artificial tear compositions comprising one or more nonionic surfactants with one or more non-Newtonian viscosity enhancing excipients.

17 Claims, No Drawings

ARTIFICIAL TEAR COMPOSITIONS COMPRISING A COMBINATION OF NONIONIC SURFACTANTS

FIELD OF THE INVENTION

The invention is directed to artificial tear compositions comprising one or more nonionic surfactants with one or more non-Newtonian viscosity enhancing excipients. The invention is further directed to a method of treating eye discomfort by administering artificial tear compositions comprising one or more nonionic surfactants with one or more non-Newtonian viscosity enhancing excipients to a subject in need thereof.

BACKGROUND OF THE INVENTION

The eye produces tears which are spread across the eye during blinking. The unique components of tears along with the blinking process create a tear film that is made up of a mucous layer, an aqueous layer and a lipid layer. This tear film evaporates, drains and is replaced by new tear film components during blinking. This unique system creates a barrier between the environment and the surface of the eye and removes any irritants that may enter the eye.

Dry eye is a common affliction that is caused by the failure of the eye to produce either an adequate amount or maintain a proper balance of tear components. In either instance the tear film that normally covers the eye becomes unstable (i.e. no longer covers the entire eye) and fails to remove irritants. These irritants cause many of the conditions associated with dry eye such as burning, stinging, itching and tired eyes. Dry eye symptoms can be exacerbated by activities that extend the time between eye blinks such as prolonged computer use and reading.

Artificial tear compositions contain polymers that act to mimic the aqueous, mucous and/or lipid layers of the tear film to maintain the stability of the film and prevent rapid evaporation. High viscosity compositions maintain a longer lasting tear film but are difficult to apply and can result in blurred vision. Low viscosity compositions do not maintain a long lasting tear film, in part, due to forces applied during blinking. Normally, blinking causes a shear force to be applied to the tear film, spreading the new tear components across the eye. This same shear force aids in the evaporation and drainage of the existing tear components. When natural tear components are being supplemented by artificial tears, repeated application of the artificial tears is necessary to replace those components that are lost due to blinking. The viscosity of the artificial tear composition has a direct correlation with the ability to withstand the shear force caused by blinking.

Currently available artificial tear compositions are deficient because they either maintain a stable tear film for a short period of time or cause blurred vision for a relatively long period of time. The longest lasting artificial tears on the market use high concentrations of viscosity enhancing agents. Celluvisc° (Celluvisc is a registered trademark of Allergan, Inc.), which uses high viscosity carboxymethyl cellulose ("CMC") 1%—about 350 centipoise (cps) viscosity, and Refresh Liquigel° (Refresh Liquigel is a registered trademark of Allergan, Inc.), which uses a blend of 0.35% high viscosity CMC and 0.65% low viscosity CMC—about 70 cps, are two such compositions. These high viscosity artificial tear compositions are long lasting but cause significantly blurred vision lasting up to 10 minutes or longer.

There is a need in the art for a long-lasting artificial tear composition that is comfortable to the user and causes a relatively short period of blurred vision upon instillation.

Additionally, there exist products on the market for cleaning contact lenses once removed from the eye. However, there is no product on the market that cleans the contact lens while in the eye. There remains a need for such a product to reduce build up and clean contact lenses while in the eye.

SUMMARY OF THE INVENTION

In certain embodiments, the present invention is directed to an artificial tear composition comprising:
1) from 0.2% to 7.0% w/v of at least one nonionic surfactant; and
2) one or more non-Newtonian viscosity enhancing excipients of high molecular weight blend having from about 1,000 centipoise (cps) to about 3,000 cps@ 1% 27 C.

In certain other embodiments, the present invention is directed to an artificial tear composition comprising:
1) from 0.2% to 7.0% w/v of at least one nonionic surfactant; and
2) from about 0.20% to about 0.80% w/v carboxymethyl cellulose ("CMC").

In certain other embodiments, the present invention is directed to an artificial tear composition comprising:
1) from 0.2% to 7.0% w/v of at least one nonionic surfactant; and
2) from about from about 0.10% to about .1.00% w/v hydroxypropylmethyl cellulose ("HPMC").

In certain other embodiments, the present invention is directed to an artificial tear composition comprising:
1) from 0.2% to 7.0% w/v of at least one nonionic surfactant; and
2) from about from about 1.0% to about 1.75% w/v hydroxypropyl cellulose ("HPC").

In certain other embodiments, the present invention is directed to an artificial tear composition comprising:
1) 0.25% w/v sodium chloride ("NaCl");
2) 0.01% w/v benzalkonium chloride ("BAK");
3) from 0.2% to 7.0% w/v of at least one nonionic surfactant; and
4) one or more non-Newtonian viscosity enhancing excipients of high molecular weight blend having from about 1,000 centipoise (cps) to about 3,000 cps.

In certain embodiments, the present invention is directed to an artificial tear composition comprising:
1) 0.25% w/v sodium chloride ("NaCl");
2) 0.01% w/v benzalkonium chloride ("BAK");
3) from about 0.1% to about 1.0% w/v of glycerin;
4) from 0.2% to 7.0% w/v of at least one nonionic surfactant; and
5) one or more non-Newtonian viscosity enhancing excipients of high molecular weight blend from 0.10% to 1.75% w/v having from about 1,000 centipoise (cps) to about 3,000 cps@ 1% 27 C.

In preferred embodiments, the present invention is directed to an artificial tear composition comprising from 4% to 5% w/v polyoxyl 40 stearate, 0.2% w/v poloxamer 407, 0.1% w/v poloxamer 188, a viscosity enhancing excipient selected from the group consisting of CMC, carboxypropylmethyl cellulose ("CPMC"), HPC, and HPMC or a combination thereof, 0.25% w/v NaCl and 0.01% w/v BAK.

In other preferred embodiments, the present invention is directed to an artificial tear composition comprising from 3.7% to 5% w/v polyoxyl 40 stearate, 0.2% w/v poloxamer 407, 0.1% w/v poloxamer 188, 1.0% w/v polysorbate 80, a viscosity enhancing excipient selected from the group consisting of CMC, CPMC, HPC, and HPMC or a combination thereof, 0.25% w/v NaCl and 0.01% w/v BAK.

In certain embodiments, the present invention is directed to a method of treating eye discomfort comprising administering an artificial tear composition comprising:
1) from 0.2% to 7.0% w/v of at least one nonionic surfactant; and
2) one or more non-Newtonian viscosity enhancing excipients of high molecular weight blend having from about 1,000 centipoise (cps) to about 3,000 cps@ 1% 27 C; to a subject in need thereof.

In preferred embodiments, the present invention is directed to a method of treating eye discomfort comprising administering an artificial tear composition comprising:
1) from 0.2% to 7.0% w/v of at least one nonionic surfactant; and
2) one or more non-Newtonian viscosity enhancing excipients of high molecular weight blend having from about 1,000 centipoise (cps) to about 3,000 cps@ 1% 27 C; to a subject in need thereof.

In other more preferred embodiments, the present invention is directed to an artificial tear composition comprising:
1) from 0.2% to 7.0% w/v of at least one nonionic surfactant; and
2) from 0.1% to 0.5% w/v of a non-Newtonian viscosity enhancing excipient;
wherein the artificial tear composition further comprises a contact lens cleaning capability.

In other embodiments, the present invention is directed to a method of treating eye discomfort comprising administering an artificial tear composition with contact lens cleaning capability comprising:
1) from 0.2% to 7.0% w/v of at least one nonionic surfactant; and
2) from 0.1% to 0.5% w/v of a non-Newtonian viscosity enhancing excipient; to a subject in need thereof.

DETAILED DESCRIPTION OF THE INVENTION

The present invention is directed to an artificial tear composition comprising:
1) from 0.2% to 7.0% w/v of at least one nonionic surfactant; and
2) one or more non-Newtonian viscosity enhancing excipients of high molecular weight blend having from about 1,000 centipoise (cps) to about 3,000 cps@ 1% 27 C.

As used herein, the term "composition" is intended to encompass a product comprising the specified ingredients in the specified amounts, as well as any product which results, directly or indirectly, from a combination of the specified ingredients in the specified amounts.

As used herein, all numerical values relating to amounts, weights, and the like, that are defined as "about" each particular value is plus or minus 10%. For example, the phrase "about 5% w/v" is to be understood as "4.5% to 5.5% w/v." Therefore, amounts within 10% of the claimed value are encompassed by the scope of the claims.

As used herein "% w/v" refers to the percent weight of the total composition.

As used herein the term "subject" refers but is not limited to a person or other animal.

Nonionic surfactants that can be used in accordance with the present invention include, but are not limited to, poloxamers, polysorbates, cyclodextrins, and polyoxyl alkyls; where preferred embodiments include but are not limited to Poloxamer 188, Poloxamer 407, Polysorbate 20, Polysorbate 80, 2-HP-cyclodextrin, Polyoxyl 40 stearate, Polyoxyl 35 castor oil, and Polyoxyl 40 hydrogenated castor oil or combinations thereof.

In preferred embodiments the nonionic surfactant is polyoxyl 40 stearate.

In more preferred embodiments the amount of polyoxyl 40 stearate is from 3.7% to 5.5% w/v.

In other preferred embodiments the artificial tear composition includes one or more additional nonionic surfactants, including polyoxyl 35 castor oil or polyoxyl 40 hydrogenated castor oil.

In other more preferred embodiments the additional nonionic surfactant is 0.2% w/v poloxamer 407.

In other more preferred embodiments the additional nonionic surfactants are 0.2% w/v poloxamer 407 and 0.10% w/v poloxamer 188.

In other more preferred embodiments the additional nonionic surfactants are 0.2% w/v poloxamer 407, 0.10% w/v poloxamer 188 and 1.0% w/v polysorbate 80.

In other more preferred embodiments the additional nonionic surfactants are 0.2% w/v poloxamer 407, 0.10% w/v poloxamer 188, 1.0% w/v polysorbate 80 and 0.05% w/v polysorbate 20.

Polyoxyl 35 castor oil is present at an amount from 0.25% to 5.00% w/v; preferably from 0.25% to 1.50% w/v; more preferably from 0.75% to 1.0% w/v.

Non-Newtonian viscosity enhancing excipients that can be used in accordance with the present invention include, but are not limited to, carboxymethyl cellulose high molecular weight blend ("CMC"), methylcellulose, methyl cellulose 4000, hydroxymethyl cellulose, hydroxypropyl cellulose ("HPC"), hydroxypropylmethyl cellulose high molecular weight blend ("HPMC"), hydroxylpropyl methyl cellulose 2906, carboxypropylmethyl cellulose high molecular weight blend ("CPMC"), hydroxyethyl cellulose, or hydroxyethyl cellulose and hyaluronic acid, such that the concentrations cumulatively do not create a phase transition to an in situ gel.

In preferred embodiments the viscosity enhancing excipient is selected from the group consisting of CMC, CPMC, HPC and HPMC or a combination thereof.

In more preferred embodiments the amount of CMC is from 0.2% to 0.8% w/v including 0.25% w/v, 0.55% w/v, 0.62% w/v or 0.75% w/v.

In other more preferred embodiments the amount of HPC is from 1.0% to 1.75% w/v including 1.0% w/v, 1.25% w/v, 1.40% w/v, 1.50% w/v or 1.75% w/v.

In other more preferred embodiments the amount of HPMC is from 0.10% to 0.75% w/v including 0.10% w/v, 0.20% w/v, 0.25% w/v, 0.3% w/v, 0.4% w/v, 0.5% w/v, 0.55% w/v, 0.62% w/v, 0.75% w/v,.

In other embodiments the present invention further comprises glycerin in an amount from 0.1% to 1.0% w/v; preferably from 0.3% to 0.4% w/v.

Preservatives that can be used in accordance with the present invention include, but are not limited to, benzalkonium chloride ("BAK"), methylparaben, polypropylparaben, chlorobutanol, thimerosal, phenylmercuric acetate, perborate, or phenylmercuric nitrate. BAK, in particular, has been found to be effective with preferred embodiments.

Buffers and pH adjustors that can be used in accordance with the present invention include, but are not limited to, acetate buffers, carbonate buffers, citrate buffers, phosphate buffers and borate buffers. It is understood that various acids or bases can be used to adjust the pH of the composition as needed. pH adjusting agents include, but are not limited to, sodium hydroxide and hydrochloric acid. Surprisingly, pH has not been found to alter comfort in the artificial tears compositions. pH of the compositions can be from 4.0 to 8.0.

Antioxidants that can be used in accordance with the present invention include, but are not limited to, sodium metabisulfite, sodium thiosulfate, acetylcysteine, butylated hydroxyanisole and butylated hydroxytoluene.

The present invention is further directed to a method of treating eye discomfort comprising administering an artificial tear composition comprising:
1) from 0.2% to 7.0% w/v of at least one nonionic surfactant; and
2) one or more non-Newtonian viscosity enhancing excipients of high molecular weight blend having from about 1,000 centipoise (cps) to about 3,000 cps@ 1% 27 C; to a subject in need thereof.

The artificial tear compositions of the present invention are suitable for administration two, three or four times per day to a subject in need thereof.

Representative Embodiments

In a more preferred embodiment the artificial tear composition comprises 5.0% w/v polyoxyl 40 stearate, 0.55% w/v carboxymethyl cellulose ("CMC"), 0.25% w/v sodium chloride ("NaCl") and 0.01% w/v benzalkonium chloride ("BAK").

In another more preferred embodiment the artificial tear composition comprises 5.0% w/v polyoxyl 40 stearate, 0.55% w/v hydroxypropylmethyl cellulose ("HPMC"), 0.25% w/v NaCl and 0.01% w/v BAK.

In another more preferred embodiment the artificial tear composition comprises 4.5% w/v polyoxyl 40 stearate, 0.2% w/v poloxamer 407, 0.55% w/v CMC, 0.25% w/v NaCl and 0.01% w/v BAK.

In another more preferred embodiment the artificial tear composition comprises 5.0% w/v polyoxyl 40 stearate, 0.2% w/v poloxamer 407, 0.55% w/v CMC, 0.25% w/v NaCl and 0.01% w/v BAK.

In another more preferred embodiment the artificial tear composition comprises 5.5% w/v polyoxyl 40 stearate, 0.2% w/v poloxamer 407, 0.55% w/v CMC, 0.25% w/v NaCl and 0.01% w/v BAK.

In another more preferred embodiment the artificial tear composition comprises 5.0% w/v polyoxyl 40 stearate, 0.2% w/v poloxamer 407, 0.10% w/v poloxamer 188, 0.55% w/v CMC, 0.25% w/v NaCl and 0.01% w/v BAK.

In another more preferred embodiment the artificial tear composition comprises 5.0% w/v polyoxyl 40 stearate, 0.2% w/v poloxamer 407, 0.10% w/v poloxamer 188, 0.62% w/v CMC, 0.25% w/v NaCl and 0.01% w/v BAK.

In another more preferred embodiment the artificial tear composition comprises 5.0% w/v polyoxyl 40 stearate, 0.2% w/v poloxamer 407, 0.10% w/v poloxamer 188, 0.75% w/v CMC, 0.25% w/v NaCl and 0.01% w/v BAK.

In another more preferred embodiment the artificial tear composition comprises 5.0% w/v polyoxyl 40 stearate, 0.2% w/v poloxamer 407, 0.10% w/v poloxamer 188, 0.25% w/v NaCl and 0.01% w/v BAK.

In another more preferred embodiment the artificial tear composition comprises 5.0% w/v polyoxyl 40 stearate, 0.2% w/v poloxamer 407, 0.10% w/v poloxamer 188, 0.1% w/v HPMC, 0.25% w/v NaCl and 0.01% w/v BAK.

In another more preferred embodiment the artificial tear composition comprises 5.0% w/v polyoxyl 40 stearate, 0.2% w/v poloxamer 407, 0.10% w/v poloxamer 188, 0.2% w/v HPMC, 0.25% w/v NaCl and 0.01% w/v BAK.

In another more preferred embodiment the artificial tear composition comprises 5.0% w/v polyoxyl 40 stearate, 0.2% w/v poloxamer 407, 0.10% w/v poloxamer 188, 0.3% w/v HPMC, 0.25% w/v NaCl and 0.01% w/v BAK.

In another more preferred embodiment the artificial tear composition comprises 5.0% w/v polyoxyl 40 stearate, 0.2% w/v poloxamer 407, 0.10% w/v poloxamer 188, 1.0% w/v polysorbate 80, 0.35% w/v HPMC, 0.25% w/v NaCl and 0.01% w/v BAK.

In another more preferred embodiment the artificial tear composition comprises 5.0% w/v polyoxyl 40 stearate, 0.2% w/v poloxamer 407, 0.10% w/v poloxamer 188, 0.4% w/v HPMC, 0.25% w/v NaCl and 0.01% w/v BAK.

In another more preferred embodiment the artificial tear composition comprises 5.0% w/v polyoxyl 40 stearate, 0.2% w/v poloxamer 407, 0.10% w/v poloxamer 188, 0.5% w/v HPMC, 0.25% w/v NaCl and 0.01% w/v BAK.

In another more preferred embodiment the artificial tear composition comprises 5.0% w/v polyoxyl 40 stearate, 0.2% w/v poloxamer 407, 0.10% w/v poloxamer 188, 0.62% w/v HPMC, 0.25% w/v NaCl and 0.01% w/v BAK.

In another more preferred embodiment the artificial tear composition comprises 5.0% w/v polyoxyl 40 stearate, 0.2% w/v poloxamer 407, 0.10% w/v poloxamer 188, 0.75% w/v HPMC, 0.25% w/v NaCl and 0.01% w/v BAK.

In another more preferred embodiment the artificial tear composition comprises 5.0% w/v polyoxyl 40 stearate, 0.2% w/v poloxamer 407, 0.10% w/v poloxamer 188, 0.25% w/v CMC, 0.25% w/v HPMC, 0.25% w/v NaCl and 0.01% w/v BAK.

In another more preferred embodiment the artificial tear composition comprises 5.0% w/v polyoxyl 40 stearate, 0.2% w/v poloxamer 407, 0.10% w/v poloxamer 188, 1.0% w/v polysorbate 80, 0.55% w/v CMC, 0.25% w/v NaCl and 0.01% w/v BAK.

In another more preferred embodiment the artificial tear composition comprises 5.0% w/v polyoxyl 40 stearate, 0.2% w/v poloxamer 407, 0.10% w/v poloxamer 188, 1.0% w/v polysorbate 80, 0.55% w/v HPMC, 0.25% w/v NaCl and 0.01% w/v BAK.

In another more preferred embodiment the artificial tear composition comprises 5.0% w/v polyoxyl 40 stearate, 0.2% w/v poloxamer 407, 0.10% w/v poloxamer 188, 1.0% w/v polysorbate 80, 0.25% w/v CMC, 0.25% w/v HPMC, 0.25% w/v NaCl and 0.01% w/v BAK.

In another more preferred embodiment the artificial tear composition comprises 5.0% w/v polyoxyl 40 stearate, 0.2% w/v poloxamer 407, 0.10% w/v poloxamer 188, 1.0% w/v polysorbate 80, 1.25% w/v hydroxypropyl cellulose ("HPC"), 0.25% w/v NaCl and 0.01% w/v BAK.

In another more preferred embodiment the artificial tear composition comprises 5.0% w/v polyoxyl 40 stearate, 0.2% w/v poloxamer 407, 0.10% w/v poloxamer 188, 1.0% w/v polysorbate 80, 1.75% w/v hydroxypropyl cellulose ("HPC"), 0.25% w/v NaCl and 0.01% w/v BAK.

In another more preferred embodiment the artificial tear composition comprises 5.0% w/v polyoxyl 40 stearate, 0.2% w/v poloxamer 407, 0.10% w/v poloxamer 188, 1.0% w/v polysorbate 80, 0.05% w/v polysorbate 20, 1.40% w/v HPC, 0.25% w/v NaCl and 0.01% w/v BAK.

In another more preferred embodiment the artificial tears composition comprises 5.0% w/v polyoxyl 40 stearate, 0.2% w/v poloxamer 407, 0.10% w/v poloxamer 188, 0.30% w/v HPMC, 0.30% w/v glycerin, 0.25% w/v NaCl and 0.01% w/v BAK.

In another more preferred embodiment the artificial tears composition comprises 5.0% w/v polyoxyl 40 stearate, 0.2% w/v poloxamer 407, 0.10% w/v poloxamer 188, 0.50% w/v CMC, 0.25% w/v NaCl and 0.01% w/v BAK.

In another more preferred embodiment the artificial tears composition comprises 5.0% w/v polyoxyl 40 stearate, 0.2% w/v poloxamer 407, 0.10% w/v poloxamer 188, 0.75% w/v CMC 0.30% w/v HPMC, 0.25% w/v NaCl and 0.01% w/v BAK.

In another more preferred embodiment the artificial tears composition comprises 0.2% w/v poloxamer 407, 0.10% w/v poloxamer 188, 0.30% w/v HPMC, 0.25% w/v NaCl and 0.01% w/v BAK.

In another more preferred embodiment the artificial tears composition comprises 0.2% w/v poloxamer 407, 0.10% w/v poloxamer 188, 0.50% w/v CMC, 0.25% w/v NaCl and 0.01% w/v BAK.

In another more preferred embodiment the artificial tears composition comprises 0.2% w/v poloxamer 407, 0.10% w/v poloxamer 188, 1.0% w/v polysorbate 80, 0.50% w/v CMC, 0.25% w/v NaCl and 0.01% w/v BAK.

In another more preferred embodiment the artificial tears composition comprises 5.0% w/v polyoxyl 40 stearate, 0.2% w/v poloxamer 407, 0.10% w/v poloxamer 188, 0.25% w/v polyoxyl 35 castor oil, 0.30% w/v HPMC, 0.25% w/v NaCl and 0.01% w/v BAK.

In another more preferred embodiment the artificial tears composition comprises 5.0% w/v polyoxyl 40 stearate, 0.2% w/v poloxamer 407, 0.10% w/v poloxamer 188, 1.0% w/v polyoxyl 35 castor oil, 0.30% w/v HPMC, 0.25% w/v NaCl and 0.01% w/v BAK.

In another more preferred embodiment the artificial tears composition comprises 5.0% w/v polyoxyl 40 stearate, 0.2% w/v poloxamer 407, 0.10% w/v poloxamer 188, 1.5% w/v polyoxyl 35 castor oil, 0.30% w/v HPMC, 0.25% w/v NaCl and 0.01% w/v BAK.

In another more preferred embodiment the artificial tears composition comprises 5.0% w/v poloxamer 407, 1.0% w/v HPC, 0.25% w/v NaCl and 0.01% w/v BAK.

In another more preferred embodiment the artificial tears composition comprises 5.0% w/v polysorbate 80, 1.5% w/v HPC, 0.25% w/v NaCl and 0.01% w/v BAK.

In another more preferred embodiment the artificial tears composition comprises 5.0% w/v poloxamer 407, 1.75% w/v HPC, 0.25% w/v NaCl and 0.01% w/v BAK.

In another more preferred embodiment the artificial tears composition described herein further comprise a contact lens cleaning capability.

While in situ gels provide enhanced efficacy with greater topical side effects, liquid viscous gels and or suspensions do so similarly with considerable vision blur and viscous induced discomfort proportional to their efficacy. Mildly viscous liquids and matrix gels such as low concentration polycarbophil suspensions less than 0.1% provide excellent vision and comfort on instillation, but at the expense of similarly enhanced efficacy. The present invention discovers a narrow range of viscosity requiring non-Newtonian viscosity excipients and nonionic surfactants where both comfort and efficacy are optimized. The ingredients and concentrations of the compositions represented herein are the best known embodiments but are not intended to be all inclusive.

Example

Artificial Tear Compositions

TABLE 1

| Efficacy of artificial tear compositiions. | | | | | | | | | |
|---|---|---|---|---|---|---|---|---|---|
| (% w/v) | 1 | 2 | 3 | 4 | 5 | 6 | 7 | 8 | 9 |
| Polyoxyl 40 stearate | 4.50% | 5.00% | 5.50% | 5.00% | 5.00% | 5.00% | 5.00% | 5.00% | 5.00% |
| Poloxamer 407 | 0.20% | 0.20% | 0.20% | 0.20% | 0.20% | 0.20% | | | 0.20% |
| Poloxamer 188 | | | | 0.10% | 0.10% | 0.10% | | | 0.10% |
| Polysorbate 80 | | | | | | | | | |
| Polysorbate 20 | | | | | | | | | |
| Polyoxyl 35 castor oil | | | | | | | | | |
| CMC | 0.55% | 0.55% | 0.55% | 0.55% | | | 0.55% | | 0.25% |
| HPC | | | | | | | | | |
| HPMC | | | | | 0.40% | 0.62% | | 0.55% | 0.25% |
| Glycerin | | | | | | | | | |
| NaCl 0.25% | √ | √ | √ | √ | √ | √ | √ | √ | √ |
| BAK 0.01% | √ | √ | √ | √ | √ | √ | √ | √ | √ |
| Visual Blur (sec) | 30-60 | 30-60 | 30-60 | 30-60 | 10 | 20-30 | 30-60 | | 10 |
| (% w/v) | 10 | 11 | 12 | 13 | 14 | 15 | 16 | 17 | 18 |
| Polyoxyl 40 stearate | 5.00% | 5.00% | 5.00% | 5.00% | 5.00% | 5.00% | 3.70% | 3.70% | 4.75% |
| Poloxamer 407 | 0.20% | 0.20% | 0.20% | 0.20% | 0.20% | 0.20% | 0.20% | 0.20% | 0.20% |
| Poloxamer 188 | 0.10% | 0.10% | 0.10% | 0.10% | 0.10% | 0.10% | 0.10% | 0.10% | 0.10% |
| Polysorbate 80 | 1.00% | 1.00% | 1.00% | | | | 1.00% | 1.00% | 1.00% |
| Polysorbate 20 | | | | | | | | | 0.05% |
| Polyoxyl 35 castor oil | | | | | | | | | |
| CMC | 0.25% | 0.55% | | | 0.75% | 0.62% | | | |
| HPC | | | | | | | 1.25% | 1.75% | 1.40% |
| HPMC | 0.25% | | 0.55% | 0.75% | | | | | |
| Glycerin | | | | | | | | | |
| NaCl 0.25% | √ | √ | √ | √ | √ | √ | √ | √ | √ |
| BAK 0.01% | √ | √ | √ | √ | √ | √ | √ | √ | √ |
| Visual Blur (sec) | 10 | | | 30-40 | 90-180 | 60-90 | 5 | 30 | 10-20 |

TABLE 1-continued

Efficacy of artificial tear compositiions.

| (% w/v) | 19 | 20 | 21 | 22 | 23 | 24 | 25 | 26 | 27 |
|---|---|---|---|---|---|---|---|---|---|
| Polyoxyl 40 stearate | 5.00% | 5.00% | | | 5.00% | 5.00% | 5.00% | 5.00% | 5.00% |
| Poloxamer 407 | 0.20% | 0.20% | 0.20% | | 0.20% | 0.20% | 0.20% | 0.20% | 0.20% |
| Poloxamer 188 | 0.10% | 0.10% | 0.10% | | 0.10% | 0.10% | 0.10% | 0.10% | 0.10% |
| Polysorbate 80 | | | | 5.00% | | | | | |
| Polysorbate 20 | | | | | | | | | |
| Polyoxyl 35 castor oil | | | | | | | | | |
| CMC | 0.50% | | | | 0.75% | | | | |
| HPC | | | | 1.50% | | | | | |
| HPMC | | | 0.30% | | 0.30% | 0.50% | 0.10% | 0.20% | 0.30% |
| Glycerin | | | | | | | | | |
| NaCl 0.25% | √ | √ | √ | √ | √ | √ | √ | √ | √ |
| BAK 0.01% | √ | √ | √ | √ | √ | √ | √ | √ | √ |
| Visual Blur | 45 | 2 | 5 | 20 | 30 | 15 | 3.5 | 5 | 5 |
| Wetting Effect (min) | 90 | 30 | 30 | 60 | 90 | 45 | 45 | 45 | 45 |
| Comfort (4 is best) | 3.5 | 3.5 | 3.0 | 3.5 | 3.5 | 3.5 | 3.5 | 3.5 | 3.5 |
| Visual Quality (4 is best) | 3.7 | 3.7 | 3.5 | 3.5 | 3.5 | 3.8 | 3.7 | 3.8 | 3.8 |
| Overall Performance | 2.0 | 3.0 | 3.0 | 3.0 | 3.1 | 3.1 | 3.2 | 3.2 | 3.2 |

| (% w/v) | 28 | 29 | 30 | 31 | 32 | 33 | 34 | 35 |
|---|---|---|---|---|---|---|---|---|
| Polyoxyl 40 stearate | | | 5.00% | | | 5.00% | 5.00% | 5.00% |
| Poloxamer 407 | 0.20% | 5.00% | 0.20% | 0.20% | 5.00% | 0.20% | 0.20% | 0.20% |
| Poloxamer 188 | 0.10% | | 0.10% | 0.10% | | 0.10% | 0.10% | 0.10% |
| Polysorbate 80 | | | | 1.00% | | | | |
| Polysorbate 20 | | | | | | | | |
| Polyoxyl 35 castor oil | | | | | | 0.25% | 1.00% | 1.50% |
| CMC | 0.50% | | | 0.50% | | | | |
| HPC | | 1.75% | | | 1.00% | | | |
| HPMC | | | 0.30% | | | 0.30% | 0.30% | 0.30% |
| Glycerin | | | 0.30% | | | | | |
| NaCl 0.25% | √ | √ | √ | √ | √ | √ | √ | √ |
| BAK 0.01% | √ | √ | √ | √ | √ | √ | √ | √ |
| Visual Blur | 45 | 40 | 7 | 15 | 20 | 0 | 1 | 1 |
| Wetting Effect (min) | 30 | 60 | 45 | 60 | 60 | 90 | 180 | 180 |
| Comfort (4 is best) | 3.0 | 3.5 | 3.7 | 3.5 | 3.5 | 4.0 | 4.0 | 4.0 |
| Visual Quality (4 is best) | 3.5 | 3.5 | 3.5 | 3.5 | 3.5 | 3.9 | 4.0 | 4.0 |
| Overall Performance | 3.2 | 3.2 | 3.5 | 3.5 | 3.5 | 3.8 | 4.0 | 4.0 |

Artificial tear compositions with at least four nonionic surfactants are most preferred, three surfactants are more preferred and those limited to one or two least preferred; a nonionic surfactant cumulative concentration of at least 5% or greater is preferred; with the order of preference of nonionic surfactants polyoxyl 40 stearate>polyoxyl 35 castor oil>poloxamer 0.20%>poloxamer 0.188%>polysorbate 80; and where polyoxyl 35 castor oil combined with polyoxyl 40 stearate provides a particularly comfortable combination on instillation . . . . Of the three surfactant compositions those with HPMC as the non-Newtonian viscosity enhancing agent are preferred over those with CMC, HPC or combinations thereof. Of the three surfactant compositions with HPMC those that additionally include polyoxyl 35 castor oil are most preferred. Compositions 33, 34, and 35 are most preferred.

Unexpected Results of Using the Specific Combinations of the Ingredients

The present invention combines a high degree of mucoadhesiveness, temperature sensitive alteration in rheological properties between and during blink allowing for physiologic blinking without blur, and after equilibration within about 15 to 60 seconds depending on the embodiment selected results on instillation creates a thin tear film of about 5-10 μm. It has been surprising that the present invention:

a) creates prolonged wetting and hydration typically of about one hour or longer;

b) creates minimal blur on instillation of tens of seconds, typically 30 seconds or less (See Table 1 above);

c) produces no crusting of lids or lashes, only a prolonged wetting action felt along lid margins; and d) allows comfortable instillations at very low (less than 4) or high (greater than 7) pH.

It has been found that deviation from the narrow range of concentrations results in either greater comfort at the expense of efficacy where lower values are used or blurred vision, viscous lid drag, surface residue but greater efficacy with longer tear surface retention where higher values are used. The inventive compositions discovered provide a very narrow range of nonionic surfactants and non-Newtonian viscosity enhancing excipients, where the benefits of an in situ gel coexist with the benefits of a low viscosity artificial tear for comfort and vision without phase transition and where only nonionic surfactants in combination with these narrow ranges optimally and surprisingly result in long lasting tear film stability without extended blurry vision upon instillation. It has also been found that a poloxamer alone, without additional excipients, regardless of concentration, is not only ineffective for the purposes of the present invention in terms of increased efficacy, but it also creates severe stinging on topical application, whether it is buffered or non-buffered, and regardless of pH.

It has been discovered that polyoxyl alkyls (e.g. polyoxyl 40 stearate, polyoxyl 35 castor oil), poloxamers, and polysorbates are effective in the provided combinations when they are present at 12% or less and preferably at more than 3% but less than 10%. When polyoxyl 40 stearate, poloxamers, and polysorbates are present at a concentration of 15% or greater or less than 2%, the compositions are surprisingly less effective or ineffective.

It was also surprising and unexpected that the use of viscosity enhancers at very low or high concentrations resulted in surprisingly more side effects and reduced efficacy, and further that preference is HPMC>HPC>CMC, where all are high density molecular weights. It has also been found that the use of viscosity enhancers by themselves (i.e., without polyoxyl 40 stearate, poloxamers, and polysorbates) results in much less effective compositions with more side effects.

Not wishing to be held to particular theory, there clearly appears to be surprising effects from the narrow concentrations and combination of particularly the number, cumulative concentration, and type of nonionic surfactants in combination with viscosity excipients which allows increased tear film stability with reduced time of blurred vision.

What is claimed is:

1. An artificial tear composition comprising:
a non-Newtonian viscosity enhancing excipient selected from the group consisting of 0.10% to 0.75% w/v hydroxypropylmethyl cellulose and 0.20% to 0.80% w/v carboxymethyl cellulose;
and at least the following nonionic surfactants: 5.0% w/v polyoxyl 40 stearate, 0.2% w/v poloxamer 407, and 0.1% w/v poloxamer 188.

2. The composition of claim 1 further comprising 0.25% w/v sodium chloride and 0.01% w/v benzalkonium chloride.

3. The composition of claim 1 wherein, hydroxypropylmethyl cellulose is at an amount of 0.10% w/v.

4. The composition of claim 1 wherein, hydroxypropylmethyl cellulose is at an amount of 0.20% w/v.

5. The composition of claim 1 wherein, hydroxypropylmethyl cellulose is at an amount of 0.30% w/v.

6. The composition of claim 1 wherein, hydroxypropylmethyl cellulose is at an amount of 0.40% w/v.

7. The composition of claim 1 wherein, hydroxypropylmethyl cellulose is at an amount of 0.50% w/v.

8. The composition of claim 1 wherein, hydroxypropylmethyl cellulose is at an amount of 0.62% w/v.

9. The composition of claim 1 wherein, hydroxypropylmethyl cellulose is at an amount of 0.75% w/v.

10. The artificial tear composition of claim 1 further comprising glycerin at an amount from about 0.1% to about 1.0% w/v.

11. An artificial tear composition comprising:
a non-Newtonian viscosity enhancing excipient selected from the group consisting of carboxymethyl cellulose, carboxypropylmethyl cellulose, hydroxypropyl cellulose, hydroxyethyl cellulose, and hydroxypropylmethyl cellulose or a combination thereof;
at least the following nonionic surfactants: 5% w/v polyoxyl 40 stearate, 0.2% w/v poloxamer 407, 0.1% w/v poloxamer 188, from 0.25% to 1.5% w/v polyoxyl 35 castor oil;
0.25% w/v sodium chloride; and
benzalkonium chloride or a perborate.

12. The artificial tear composition of claim 11, wherein polyoxyl 35 castor oil is 0.25% w/v and the viscosity enhancing excipient is 0.30% w/v hydroxypropylmethyl cellulose.

13. The artificial tear composition of claim 11, wherein polyoxyl 35 castor oil is 1.00% w/v and the viscosity enhancing excipient is 0.30% w/v hydroxypropylmethyl cellulose.

14. The artificial tear composition of claim 11, wherein polyoxyl 35 castor oil is 1.50% w/v the viscosity enhancing excipient is 0.30% w/v hydroxypropylmethyl cellulose.

15. A method of treating eye discomfort comprising administering the artificial tear composition of claim 1 to a subject in need thereof.

16. A method of treating eye comprising administering the artificial tear composition of claim 11 to a subject in need thereof.

17. A method of cleaning a contact lens comprising contacting a contact lens with the artificial tear composition of claim 11.

* * * * *